(12) United States Patent
Arifin et al.

(10) Patent No.: US 9,415,131 B2
(45) Date of Patent: Aug. 16, 2016

(54) ENHANCED PHOTOOXIDATION REACTOR AND PROCESS

(71) Applicant: Evoqua Water Technologies Pte. Ltd., Warrendale, PA (US)

(72) Inventors: Davis Yohanes Arifin, Singapore (SG); Richard Woodling, Singapore (SG); Rajeshkumar Rajendran, Singapore (SG)

(73) Assignee: Evoqua Water Technologies Pte. Ltd, Singapore (SG)

( * ) Notice: Subject to any disclaimer, the term of this patent is extended or adjusted under 35 U.S.C. 154(b) by 0 days.

(21) Appl. No.: 14/430,565

(22) PCT Filed: Mar. 15, 2013

(86) PCT No.: PCT/US2013/032139
§ 371 (c)(1),
(2) Date: Mar. 24, 2015

(87) PCT Pub. No.: WO2014/058471
PCT Pub. Date: Apr. 17, 2014

(65) Prior Publication Data
US 2015/0250914 A1    Sep. 10, 2015

Related U.S. Application Data

(60) Provisional application No. 61/713,173, filed on Oct. 12, 2012, provisional application No. 61/713,821, filed on Oct. 15, 2012, provisional application No. 61/714,498, filed on Oct. 16, 2012.

(51) Int. Cl.
*A61L 9/20* (2006.01)
*B01D 53/00* (2006.01)
*B01D 53/88* (2006.01)
*B01J 19/12* (2006.01)

(52) U.S. Cl.
CPC .............. *A61L 9/205* (2013.01); *B01D 53/007* (2013.01); *B01D 53/885* (2013.01); *B01D 2255/802* (2013.01); *B01D 2257/90* (2013.01); *B01D 2259/804* (2013.01); *B01J 19/123* (2013.01); *B01J 2219/0875* (2013.01); *B01J 2219/0892* (2013.01); *C02F 2303/02* (2013.01)

(58) Field of Classification Search
CPC ................. B01J 19/12; A61L 9/205
See application file for complete search history.

(56) References Cited

U.S. PATENT DOCUMENTS

| | | | |
|---|---|---|---|
| 5,835,840 A * | 11/1998 | Goswami | A61L 9/20 422/186.3 |
| 2009/0020016 A1 * | 1/2009 | Christophersen et al. | 96/224 |
| 2011/0064638 A1 * | 3/2011 | Molins | 423/245.1 |
| 2011/0318237 A1 * | 12/2011 | Woodling et al. | 422/186.3 |

* cited by examiner

*Primary Examiner* — Sean E Conley

(57) ABSTRACT

Aspects and embodiments of the present disclosure are directed to apparatus and methods for the photooxidation of sulfur-containing contaminants in air. In one example, an odor control system comprises a source of air contaminated with a sulfur-containing compound and a UV oxidation reactor having an inlet in fluid communication with the source of contaminated air. The reactor includes a source of UV radiation disposed within the reactor and a reflective coating disposed on internal surfaces of the reactor.

20 Claims, 17 Drawing Sheets

ENHANCED PHOTOOXIDATION REACTOR AND PROCESS

RELATED APPLICATIONS

This application claims priority under 35 U.S.C. §119(e) to U.S. Provisional Application Ser. No. 61/713,173, titled "USE OF A REFLECTIVE COATING TO IMPROVE THE PHOTOCATALYTIC ACTIVITY OF A GASEOUS OXIDATION PROCESS," filed on Oct. 12, 2012, U.S. Provisional Application Ser. No. 61/714,498, titled "METHODS OF CATALYST PATTERNED DEPOSITION TO INCREASE CATALYTIC SURFACE AREA," filed on Oct. 16, 2012, and U.S. to Provisional Application Ser. No. 61/713,821, titled "NOVEL REACTOR DESIGN FOR ENHANCED PHOTOCATALYTIC PROCESS," filed on Oct. 15, 2012, each of which being herein incorporated by reference in its entirety.

BACKGROUND

Many undesirable airborne contaminants may be oxidized by exposure to actinic radiation, for example, ultraviolet (UV) light. Reactors for oxidizing airborne contaminants with ultraviolet light may be constructed by providing a chamber including a source of ultraviolet light through which air including contaminants to be oxidized may pass.

SUMMARY

In accordance with an aspect of the present disclosure there is provided an odor control system. The odor control system comprises a source of air contaminated with a sulfur-containing compound and a UV oxidation reactor having an inlet in fluid communication with the source of contaminated air. The reactor includes a source of UV radiation disposed within the reactor and a reflective coating disposed on internal surfaces of the reactor.

In accordance with some embodiments the source of air comprises a wastewater treatment plant.

In accordance with some embodiments the reflective coating comprises porous PTFE.

In accordance with some embodiments the reflective coating has a reflectivity of greater than about 97% for UV radiation.

In accordance with some embodiments the system further comprises a source of moisture in fluid communication with the inlet.

In accordance with some embodiments the source of UV radiation is a source of UV-C radiation.

In accordance with some embodiments the sulfur-containing compound comprises $H_2S$.

In accordance with some embodiments the source of UV-C radiation provides sufficient UV-C radiation to oxidize sufficiently all $H_2S$ in air having a concentration of $H_2S$ of between about 60 ppm and about 70 ppm within about two seconds.

In accordance with some embodiments the reactor further comprises a baffle which is substantially transparent to UV radiation.

In accordance with some embodiments the baffle is at least partially coated with a layer of photocatalyst which is substantially transparent to UV radiation.

In accordance with another aspect of the present disclosure there is provided method of facilitating the oxidation of a sulfur-containing contaminant in air. The method comprises providing a photooxidation reactor including a source of actinic radiation disposed within the reactor and a reflective coating including porous PTFE disposed on internal surfaces of the reactor. The method further comprises providing instructions to direct air contaminated with the sulfur-containing contaminant from a source of the contaminated air into the photooxidation reactor.

In accordance with some embodiments providing the instructions comprises providing instructions to direct contaminated air from a wastewater treatment plant into the photooxidation reactor.

In accordance with some embodiments the method further comprises providing instructions to control the humidity of the contaminated air directed into the photooxidation reactor to be within a predetermined range.

In some embodiments the predetermined range is between about 30% and about 95% relative humidity.

In accordance with some embodiments providing the photooxidation reactor including the source of actinic radiation disposed within the reactor comprises providing the photooxidation reactor including a source of UV-C radiation disposed within the reactor.

In accordance with some embodiments the method further comprises providing instructions to monitor a concentration of the sulfur-containing contaminant in air output from the photooxidation reactor and to adjust an operating parameter of the photooxidation reactor responsive to the concentration of the sulfur-containing contaminant being above a predetermined set point.

In some embodiments the predetermined set point is between about 5 ppm and 100 ppm of $H_2S$.

In accordance with another aspect of the present disclosure there is provided reactor for the oxidation of sulfur-containing contaminants in air with actinic radiation. The reactor comprises an inlet and an outlet, a source of actinic radiation disposed within the reactor. a source of moisture in fluid communication with the inlet, and a reflective coating including porous PTFE disposed on internal surfaces of the reactor.

In accordance with some embodiments the reactor further comprises a baffle which is substantially transparent to UV radiation.

In accordance with some embodiments the baffle is at least partially coated with a layer of photocatalyst which is substantially transparent to UV radiation.

In accordance with another aspect there is provided a method of facilitating a reduction in power to a photooxidation reactor to achieve a desired rate of contaminant oxidation. The method comprises coating internal surfaces of the photooxidation reactor with a reflective coating, the photooxidation reactor including the internal surfaces coated with the reflective coating exhibiting an equivalent rate of oxidation of one or more airborne contaminants with UV power reduced by between about 30% and about 50% as compared to a photooxidation reactor of a similar design but not including the reflective coating.

In some embodiments the method further comprises reducing a number of UV lamps in the photooxidation reactor by between about 30% and about 50%, the photooxidation reactor including the reduced number of UV lamps exhibiting an equivalent rate of oxidation of one or more airborne contaminants as compared to a reactor of a similar design but not including the reflective coating and not having a reduced number of UV lamps.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component to may be labeled in every drawing. In the drawings.

DETAILED DESCRIPTION

Figure 1A:
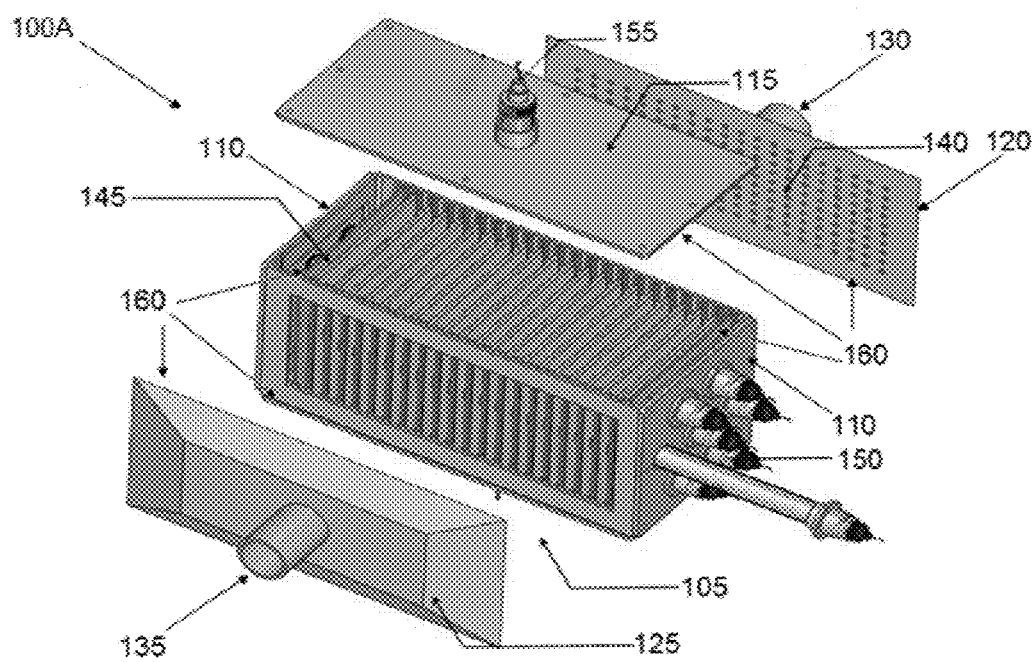
FIG. 1A is an exploded view of a reactor in accordance with an embodiment of the present disclosure.

This disclosure is not limited in its application to the details of construction and the arrangement of components set forth in the following description or illustrated in the drawings. The disclosure is capable of other embodiments and of being practiced or of being carried out in various ways.

Aspects and embodiments of the present disclosure are directed to reactors for the treatment of gas, for example, air to oxidize undesirable airborne contaminants by exposure to actinic radiation or to convert the contaminants to less undesirable substances. The actinic radiation may include UV light, however, aspects of the present disclosure are not limited to utilizing UV light. Both longer or shorter wavelengths of electromagnetic radiation or other forms of radiation may additionally or alternatively be used in aspects of reactors disclosed herein. A non-limiting list of contaminants which may be oxidized in aspects of the reactors disclosed herein includes volatile organic compounds, nitrogen dioxide, hydrogen cyanide, hydrogen sulfide, formaldehyde, sulfur-containing compounds such as organic or inorganic mercaptans, thiols, or thioethers, and microorganisms, for example, bacteria, viruses, molds, fungi, and spores. Gas including one or more of these contaminants which is treated in embodiments of the reactors described herein may be provided from, for example, biological wastewater treatment systems and/or biological sludge to dewatering systems, although gas containing contaminants from any of a number of different sources may be treated in embodiments of the reactors described herein. Sulfur-containing compounds, for example, hydrogen sulfide, organic or inorganic mercaptans, thiols, or thioethers may be present in significant concentrations in contaminated air from biological wastewater treatment systems and/or biological sludge dewatering systems.

Aspects and embodiments of reactors in accordance with the present disclosure may include catalysts which enhance the kinetics of oxidation of contaminants when exposed to actinic radiation. Various aspects and embodiments of the reactors disclosed herein may additionally or alternatively be used for the removal or oxidation of contaminants from a liquid, for example, water.

The oxidation kinetics of a photocatalytic oxidation process may depend on the catalyst density and the radiation intensity in a reactor chamber. In general, the more catalyst surface area available and the more radiation (for example, light) distributed, the greater the rate of oxidation and the greater the rate of the oxidation of contaminants. In various aspects and embodiments of the present disclosure a reflective coating technology is applied to internal surfaces of a photocatalytic reactor. The reflective coating may enhance gas-phase oxidation of contaminants in the reactor. In some embodiments the reflective coating is able to reflect about 99% of UV light energy used as actinic radiation in the reactor. Thus, almost all the UV light energy emitted from UV lamps of the reactor can be maintained to perform oxidation reactions. In water-based applications, it was determined that the contaminant oxidation rate using a reactor including reflective internal surfaces can be two to three times greater than observed in a similar reactor without a reflective coating. Since UV light transmits to a much greater degree in air (the adsorption coefficient in air is much lower than that of water), it is expected that even greater improvement can be made in photooxidation reactors used for gaseous phase contaminant removal.

Reflective coatings utilized in various embodiments disclosed herein may include, for example, a layer of polytetrafluoroethylene (PTFE). The PTFE layer may have a porous or fibrous morphology which enhances the reflectance of the material as compared to a non-porous or non-fibrous layer of PTFE. The PTFE layer may to provide diffuse reflectivity of UV radiation. Examples of such reflective PTFE material include, for example, Gore™ DRP® PTFE Diffuse Reflectors (W. L. Gore & Associates) and Optical PTFE (Berghof Products & Instruments GmbH). The reflective PTFE layer may have a thickness of, for example, between about 0.25 mm and about 3 mm and may have a UV light reflectivity of 97% or greater, and in some embodiments, greater than 99%.

It has been found that coating internal surfaces of a photo-oxidation reactor with a reflective coating, for example, porous PTFE significantly enhances the ability of the reactor to oxidize airborne contaminants. In some reactor designs it has been found that modifying the reactor to include internal surfaces coated with a reflective coating may provide for the modified reactor to achieve an equivalent contaminant oxidation performance as a reactor of the same design but unmodified to include the reflective coating with a lower power input to the UV lamps, for example a power input of between about 30% and about 50% less. Additionally or alternatively, modifying the reactor to include internal surfaces coated with a reflective coating may provide for the modified reactor to achieve an equivalent contaminant oxidation performance as a reactor of the same design but unmodified to include the reflective coating with a reduced number of UV lamps, for example, between about 30% and about 50% fewer UV lamps. In some reactor designs, coating internal surfaces of the reactor with a reflective coating may provide for the number of lamps in the reactor to be reduced from, for example, six to three or four, while achieving the same contaminant oxidation performance as an unmodified reactor of similar design.

In some embodiments, a photocatalytic reactor is provided with an increased catalyst surface area by depositing the photocatalyst in the form of a square or line pattern in which millimeter or micrometer scale features provide the additional surface area. Several photocatalyst patterning configurations are presented that have shown a catalytic surface availability improvement of, for example, from about 10% to about 60%. This catalytic surface availability improvement may result in the oxidation rate of a photocatalytic reactor to be enhanced by, for example, from about 10% to about 60%. This increase in oxidation rate may result in a smaller required reactor design for a desired amount of contaminants to be removed, providing for reduced capital and operation costs associated with the reactor.

In some embodiments, a photocatalytic reactor is provided with novel advanced photocatalytic materials. These may be in the form of nano-fibers, nano-particles, and others. These catalysts have been experimentally proven to enhance photocatalytic activity by from about 50% to about 80% as compared to a conventional process without catalyst. However, the use of these catalysts for practical applications such as oxidation of odor causing compounds in gases has previously been overlooked. As a result, there presently is no reactor design available to take advantage of the potential offered by these catalysts to improve photocatalytic processes. Aspects and embodiments of the reactor designs disclosed herein facilitate contact between a gas as the reactant, UV light radiation, and the catalyst to achieve an enhanced photocatalytic process. When operating embodiments of the photooxidation reactors disclosed herein for the removal of odor causing contaminants from air, there will be a minimum amount of harmful by-products due to most of the odor causing compounds, for example, hydrogen sulfide, being fully oxidized to $SO_4^{-2}$ ions and water vapor.

Aspects and embodiments of photooxidation reactors described herein can be used for a variety of applications. For example, they may be used for the oxidation of odor causing compounds found in a gaseous phase. They may also be used for the oxidation of organic contaminants such as endocrine disruptors or low concentrations of urea found in liquids. This disclosure is not limited to any one type of reactor design or to any particular use thereof.

Figure 1B:
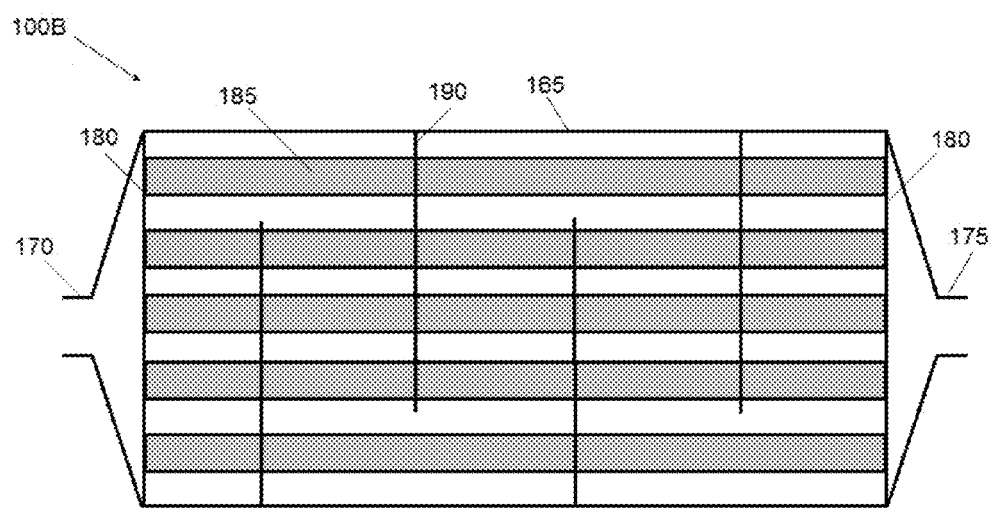
FIG. 1B is a cross sectional view of another reactor in accordance with an embodiment of the present disclosure.

A reactor for the oxidation of airborne contaminants is illustrated in an exploded view indicated generally at 100 in FIG. 1A. The reactor 100 includes a reactor body 105. The reactor body is defined by and enclosed by side walls 110, a top cover 115, a bottom cover (not visible in FIG. 1) which, in some embodiments is substantially similar to the top cover, an inlet cover 120, and an outlet cover 125. The reactor body 105 may be substantially rectangular in cross section in a plane normal to the direction of fluid flow through the reactor. The reactor 100 also includes an inlet 130 in the inlet cover 120 for the introduction of fluid, for example, air or another gas and an outlet 135 in the outlet cover 125 for the fluid to exit the reactor. to Flow of fluid through the reactor may be facilitated by, for example, a fan or blower positioned upstream of the inlet 130, downstream of the outlet 135, or both. The inlet cover 120 includes a distributor plate 140 having a plurality of air holes, which in use facilitates a uniform flow distribution of air introduced into the reactor through the inlet 130 through the reactor 100. The components of the reactor may be formed from a metal, for example, aluminum or stainless steel, or a plastic, for example, high density polyethylene (HDPE). Aspects of the reactor are not limited to any particular materials of construction unless explicitly specified in the claims.

The reactor body 105 includes a plurality of baffles 145. The baffles 145 are generally parallel to one another and to the direction of fluid flow through the reactor. The baffles 145 may be substantially identical to one another. The baffles 145 may be flat plates which are parallel to the side walls 110 to provide for fluid to flow in a straight line through the body 105 of the reactor. In alternate embodiments, one or more of the baffles may be curved, undulated, or pleated rather than in the form of flat plates. The baffles 145 may be formed of metal, glass, plastic, paper, cloth, fiber, or other materials suitable for the support of a reflective coating and/or catalyst as will be described below. The baffles 145 may have a thickness of, for example, between about 0.05 cm and about 0.2 cm, and may be spaced from another by a distance of, for example, between about 0.05 cm and about 5 cm. The reactor 100 may include, for example, between about 20 and about 100 baffle plates.

The baffles 145 may include openings through which sources of actinic radiation may pass, for example, the UV lamps included in the UV lamp assembly 150 illustrated in FIG. 1A. The UV lamp assembly 150 is illustrated as including seven tube shaped UV lamps, one of which is illustrated extending from its operational position in the body. The UV lamps are oriented normal to the surfaces of the baffles 145. The flow of fluid through the reactor is in a cross flow mode across the UV lamps. In different embodiments different numbers, for example, from one to about 10 or more lamps may be utilized. In alternate embodiments, the UV lamps may be shaped differently than illustrated, for example as U-shaped or circular lamps.

The UV lamps may emit UV-C radiation in a range of wavelengths between about 100 nm to about 280 nm, and in some embodiments, at wavelengths of 185 nm to and/or 254 nm. An example of a UV lamp utilized in some embodiments is a NIQ60/35 lamp (Heraeus Noblelight LLC). The UV lamps may provide about 6 Watts (W) of UV light power at 185 nm and 24 W of UV light power at 254 nm for a total of about 30 W of UV light power each. A plurality, for example, six lamps may be utilized in embodiments of reactors disclosed herein for a total UV power emission of about 24 W and a UV power density of about 4 W per cubic meter of reactor volume. The source of actinic radiation may additionally or alternatively include different forms of lamps or emitters, for example, photodiodes, optical fibers, or waveguides coupled to an external source of radiation.

In some embodiments, a sensor assembly 155, for example, one or more UV light sensors may be included in one of the walls of the reactor, for example, the top cover, or internal to the reactor, to provide an indication of whether the source of actinic radiation is properly functioning.

In an alternate embodiment, a UV reactor may be configured such that fluid (for example, air or another gas) flow through the reactor is substantially parallel to a long dimension of the UV lamps. An example of such a reactor, indicated generally at 100B, is illustrated in a schematic cross section in FIG. 1B. The reactor 100B may include a body 165 with an inlet 170 and an outlet 175. Distributor plates 180 may be present between the inlet 170 and/or outlet 175 and the reactor body to provide an even distribution of fluid flow into and/or out of the reactor. The reactor body may include a plurality of UV lamps 185. One or more baffles 190 may be present in the reactor body. The baffles 190 may force fluid to flow through the reactor in a serpentine manner, which may increase the residence time of fluid in the reactor, provide for mixing of the fluid, and/or facilitate a more even UV radiation exposure throughout the volume of the fluid.

Embodiments of UV reactors as disclosed herein may include various features to enhance the ability of actinic radiation supplied to the internal portion of the reactor to deactivate or oxidize contaminants. For example, a reflective coating 160 may be applied to one or more inner surfaces of the reactor. The reflective coating 160 may be applied to one or more inner surfaces of a reactor. For example, the reflective coating may be applied one or more of the top cover 115, the bottom cover, side walls 110, inlet cover 120, outlet cover 125, and/or portions of the baffles 145 of the reactor 100A of FIG. 1A. The reflective coating 160 may be in the of a flexible plastic, for example polytetrafluoroethylene (PTFE), titanium dioxide or a compound including titanium dioxide, or a rigid cold mirror formed by, for example, polishing the interior surfaces of the reactor when such surfaces are formed of a metal. Different reflective coatings may be utilized on different internal surface of the reactor 100.

In accordance with some aspects of the present disclosure, photooxidation of contaminants in a reactor may be enhanced by the addition of a photocatalyst to the interior of the reactor. Suitable photocatalysts may include, for example, any one or more of titanium dioxide ($TiO_2$), zinc oxide ($ZnO$), calcium titanium oxide ($CaTiO_3$), tin oxide ($SnO_2$), molybdenum oxide ($MnO_3$), iron oxide ($Fe_2O_3$), tungsten oxide ($WO_3$), niobium oxide ($Nb_2O_5$), silicon carbide ($SiC$), and titanium zirconium oxide ($Ti_x(Zr_{1-x})O_2$, where x has a value between zero and one). The catalysts may be in the form of nano-fibers, for example, spun titanium dioxide (Ube Material Industries, Ltd.) or nano-particles, for example, Degussa P25 titanium dioxide (Evonik-Degussa GmbH). Cocatalysts may be used in conjunction with the one or more photocatalysts to enhance the kinetics of the oxidation of contaminants. Suitable cocatalysts may include, for example, any one or more of platinum (Pt), palladium (Pd), ruthenium (Ru), silver (Ag), copper (Cu), tungsten (W), rhodium (Rh), molybdenum (Mo), gold (Au), iron (Fe), and the oxides and sulfides of these metals. Other known photocatalysts and/or cocatalysts may additionally or alternatively be utilized in various embodiments of the reactors disclosed herein. References to a photocatalyst or catalysts herein should be understood as encompassing one or more photocatalysts and optionally one or more cocatalysts.

In some embodiments, a photocatalyst may be evenly distributed over a baffle 145 of a photocatalytic reactor, such as reactor 100A. Alternatively, a baffle 145 may be formed from a photocatalytic material. Such a baffle having an even distribution of photocatalyst is illustrated in both an isometric and a side view in FIG. 2A, generally indicated at 200. In a particular embodiment, this baffle has a catalyst surface area of 380 $cm^2$. The baffle of FIG. 2A may be enhanced by adding catalyst features which may increase the surface area of catalyst available for contact with contaminants.

Figure 2A:
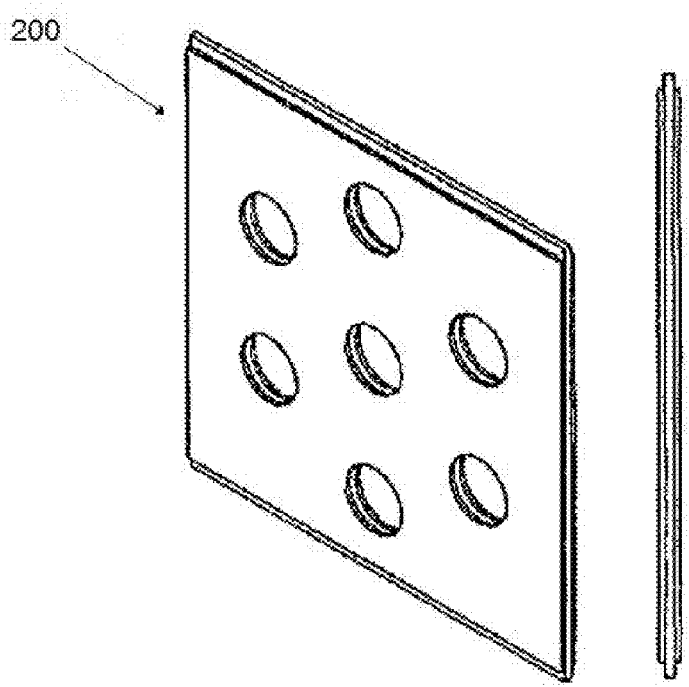
FIG. 2A is an illustration of a baffle which may be utilized in a reactor in accordance with an embodiment of the present disclosure.
Figure 2B:
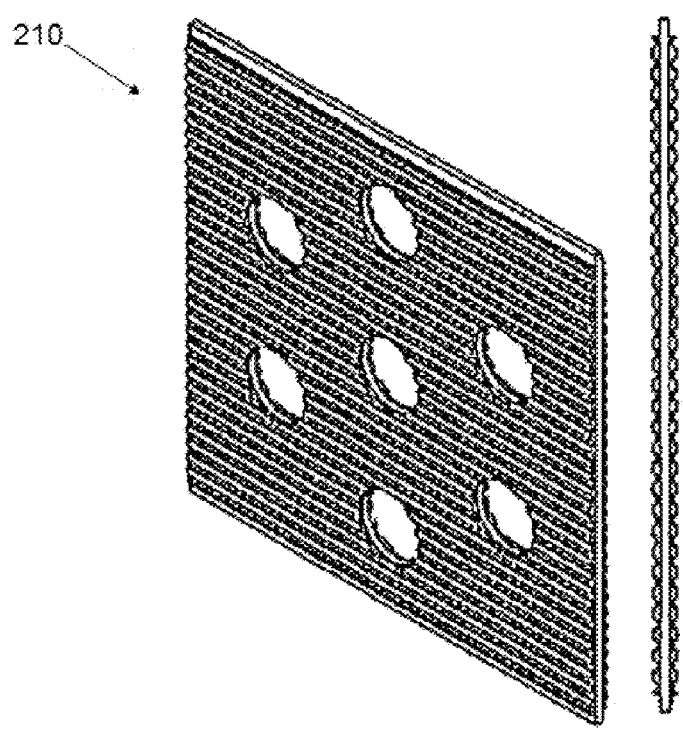
FIG. 2B is an illustration of another baffle which may be utilized in a reactor in accordance with an embodiment of the present disclosure.
Figure 2C:
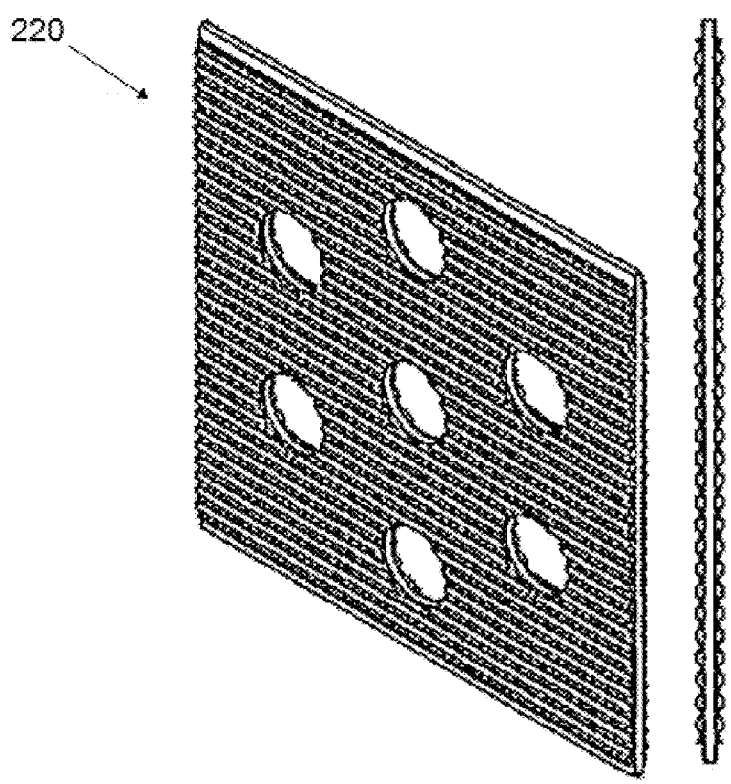
FIG. 2C is an illustration of another baffle which may be utilized in a reactor in accordance with an embodiment of the present disclosure.
Figure 2D:
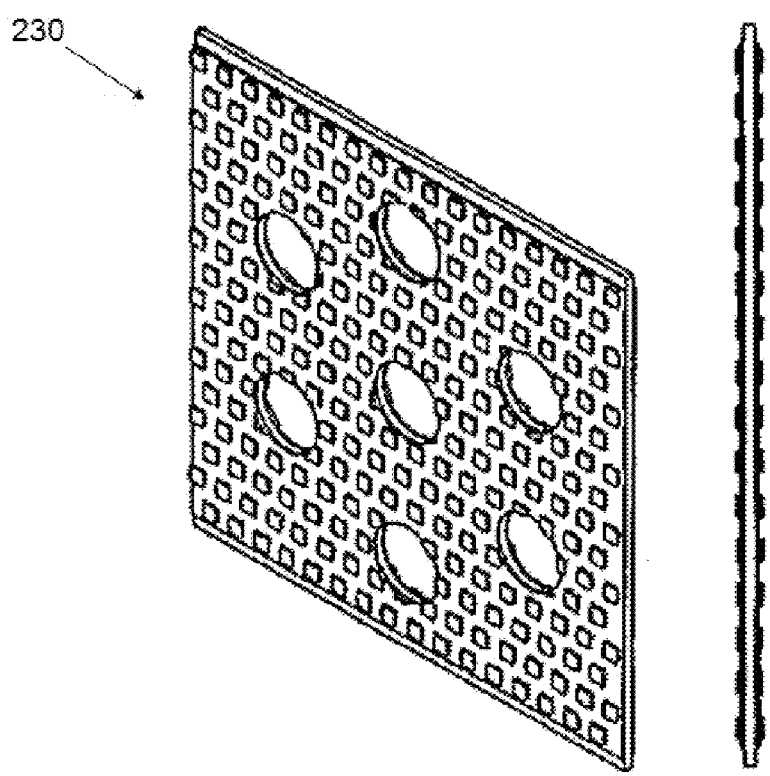
FIG. 2D is an illustration of another baffle which may be utilized in a reactor in accordance with an embodiment of the present disclosure.
Figure 2E:
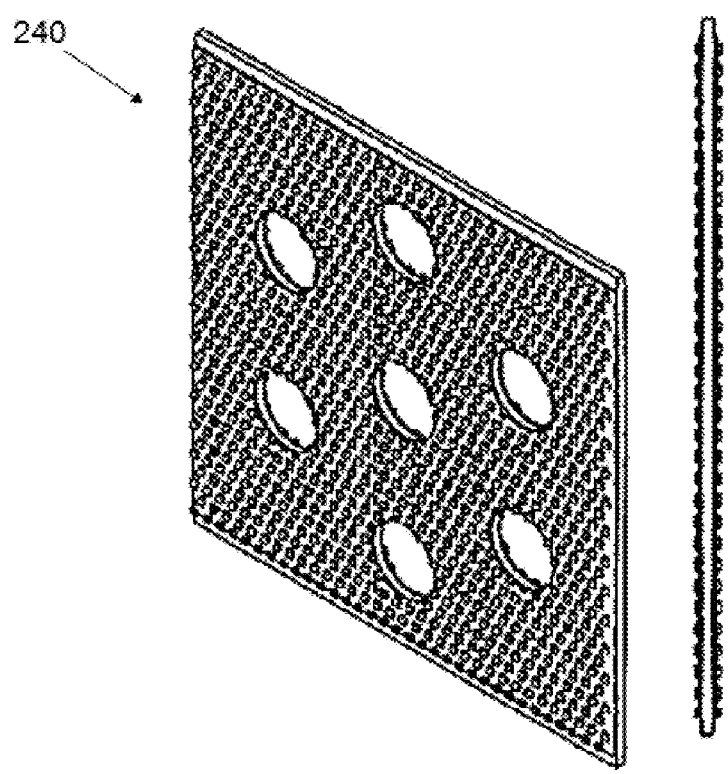
FIG. 2E is an illustration of another baffle which may be utilized in a reactor in accordance with an embodiment of the present disclosure.
Figure 2F:
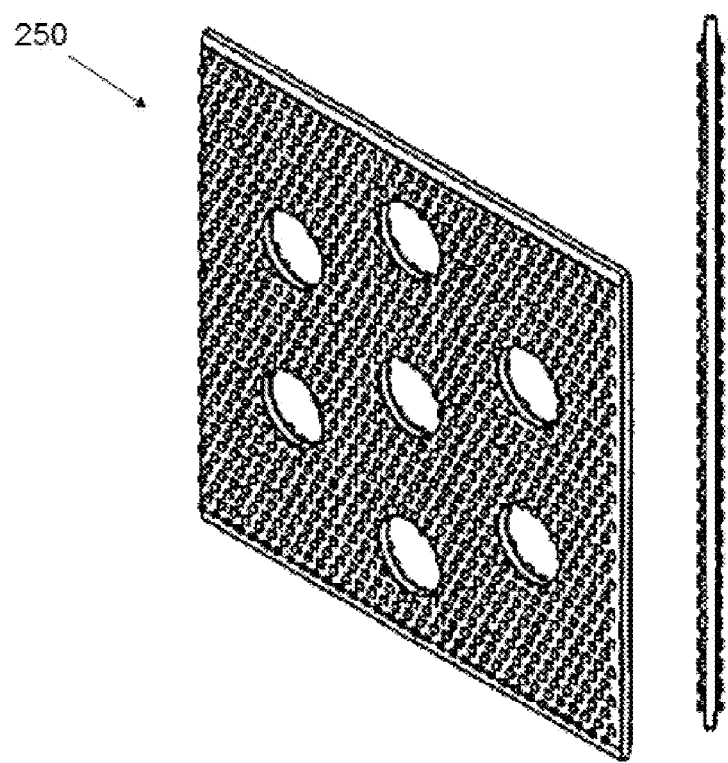
FIG. 2F is an illustration of another baffle which may be utilized in a reactor in accordance with an embodiment of the present disclosure.

In an enhancement to the baffle of FIG. 2A, a baffle 210 (FIG. 2B), having the same dimensions as the baffle of FIG. 2A, but with additional catalyst provided in lines spanning the baffle and having dimensions of 3 mm across×3 mm high with a 3 mm gap between adjacent lines has a catalyst surface area of 500 $cm^2$, an increase of 31% from the baffle of FIG. 2A. FIGS. 2C-2F illustrate alternative methods of patterning catalyst to increase the total surface area of catalyst on a baffle without increasing the size of the baffle. FIG. 2C illustrates a baffle 220 having additional catalyst provided in lines spanning the baffle and having dimensions of 1.5 mm across×1.5 mm high with a 1.5 mm gap between adjacent lines for a catalyst surface area of 624 $cm^2$, an increase of 64% from the baffle of FIG. 2A. FIG. 2D illustrates a baffle 230 having additional catalyst provided in a checker pattern of an array of squares having dimensions of 6 mm per side×6 mm high with a 6 mm gap between adjacent squares for a catalyst surface area of 427 $cm^2$, an increase of 12.5% from the baffle of FIG. 2A. FIG. 2E illustrates a baffle 240 having additional catalyst provided in a checker pattern of an array of squares having dimensions of 3 mm on a side×3 mm high with a 3 mm gap between adjacent squares for a catalyst surface area of 484 $cm^2$, an increase of 27% from the baffle of FIG. 2A. FIG. 2F illustrates a baffle 250 having additional catalyst provided in a checker pattern of an array of squares having dimensions of 1.5 mm on a side×1.5 mm high with a 1.5 mm gap between adjacent squares for a catalyst surface area of 590 $cm^2$, an increase of 55% from the baffle of FIG. 2A.

Regardless of the pattern type, a smaller feature size and/or pitch may increase the available catalyst surface area more than a larger feature size and/or pitch. Micro-patterning deposition of catalyst features on a baffle plate may thus enhance the catalyst surface area (and oxidation rate of a reactor including baffles with micro-patterned catalyst features) significantly. For example, for a baffle plate having dimensions of 190 mm×200 mm, a patterning of cubes having dimensions of 100 μm on a side will increase the available catalyst surface area as compared to a baffle deposited with a flat layer of catalyst from 380 $cm^2$ to 1,140 $cm^2$, an increase of about 200%. The catalyst surface area can be further enhanced by increasing the height of the patterned features.

The patterning configurations presented in FIGS. 2B-2F illustrate catalytic surface availability increases of between about 10% and about 60% as compared to a similarly sized flat plate baffle with a flat deposited layer of catalyst. The utilization of baffle plates having such enhanced catalyst patterning may enhance the photooxidation rate of a reactor in which they are installed by an amount commensurate with their increased catalyst surface area. A reactor utilizing baffle plates having such enhanced catalyst patterning may be constructed with a smaller size than a reactor having flat plate baffles with flat deposited layers of catalyst, for example, with up to about 60% smaller volume and achieve a same rate of contaminant oxidation as the reactor having flat plate baffles with flat deposited layers of catalyst.

Figure 3:
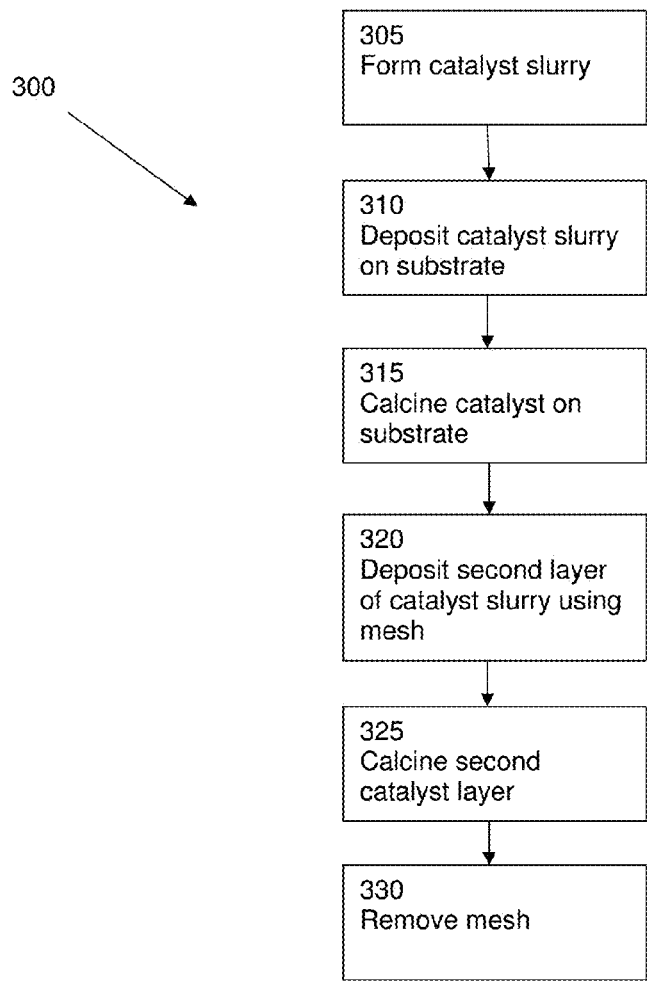
FIG. 3 is a flowchart of a method in accordance with an embodiment of the present disclosure.

The pattern of catalyst features illustrated in any of FIGS. 2A-2F may be deposited on a baffle utilizing a pre-fabricated mesh or screen as a printing tool. An embodiment of this method of catalyst feature deposition is illustrated in the flowchart of FIG. 3, indicated generally at 300. In a first act 305, a nanocrystalline powder including photocatalytic material and optionally cocatalytic material or precursors for these materials is dissolved in a fluid, for example, water or an organic solvent, and sonicated for period of time, for example, for about an hour to about two hours to form a stable catalyst slurry. In act 310 the stable catalyst slurry is deposited by, for example, a brush, by air spraying, or by a stencil blade, on a substrate for a baffle, for example, a quartz glass or stainless steel plate to form a first catalytic layer. In act 315 the substrate with the first catalytic layer undergoes a calcination process in an oven at a temperature of, for example, between about 450° C. and about 800° C. for a time period of, for example, four hours. The calcination temperature and time may vary depending upon the catalyst selected. In act 320, after the first catalytic layer has been calcined, a pre-fabricated mesh or screen is introduced on top of the first catalytic layer and additional stable catalyst slurry is deposited into apertures in the mesh or screen, for example, using a screen printing process. This forms the second catalytic layer. The second catalytic layer includes features which follow the shape and dimensions of the apertures in the pre-fabricated mesh or screen. In act 325 the to second catalytic layer undergoes a calcination process. This calcination process may be at the same or a different time and/or temperature as the calcination process for the first catalyst layer. In act 330 the mesh or screen is lifted up and removed from the calcined second layer of catalyst. The patterned substrate may then be installed and used in a photocatalytic reactor.

Figure 4:
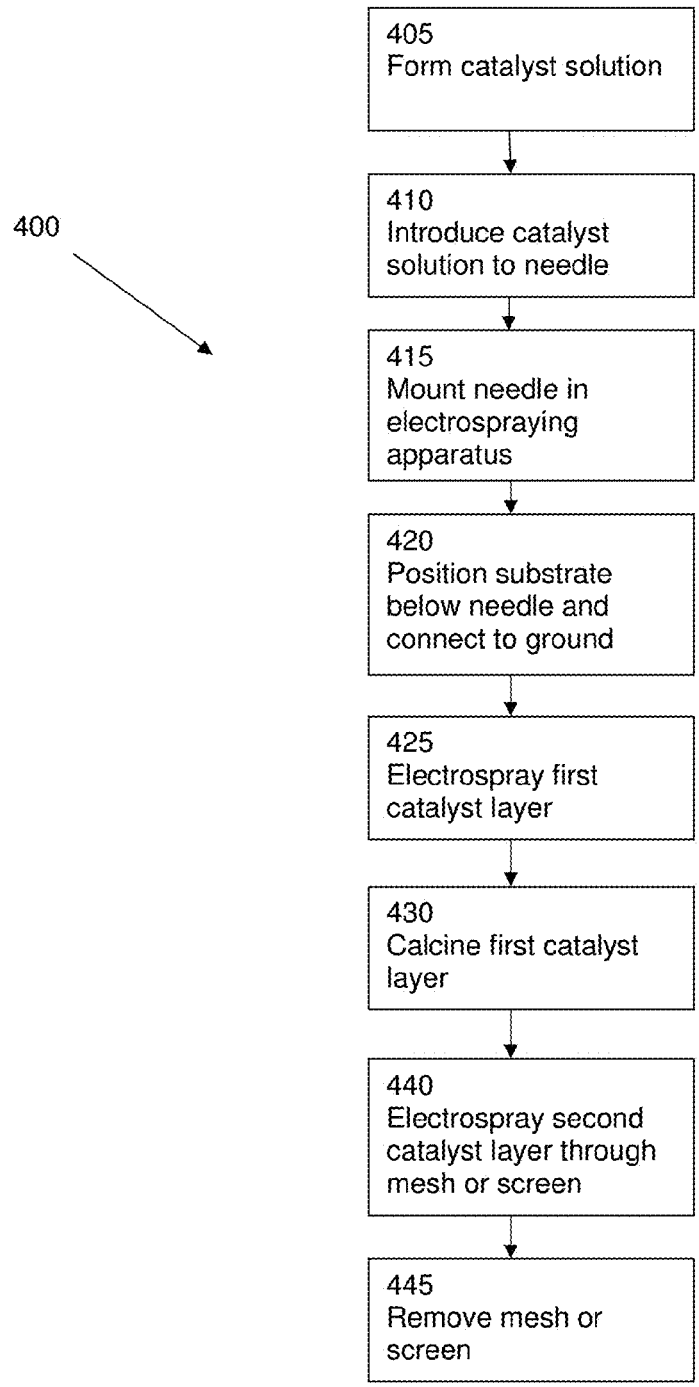
FIG. 4 is a flowchart of another method in accordance with an embodiment of the present disclosure.

A second method of forming the catalyst features illustrated in any of FIGS. 2A-2F involving electrospraying deposition is illustrated in the flowchart of FIG. 4, indicated generally at 400. In act 405, a nanocrystalline powder including photocatalytic material and optionally cocatalytic material or precursors for these materials is dissolved in a fluid, for example, water or an organic solvent, and sonicated for period of time, for example, for about an hour to about two hours to form a stable catalyst slurry or solution. The concentration of the catalyst may be adjusted to avoid potential agglomeration during electrospraying. In act 410 the catalyst solution is introduced to a syringe with a needle which will act as a mm-scale nozzle during electrospraying. In act 415 the syringe is positioned in a flow controller of an electrospraying apparatus which is configured to control the electrospraying rate. The needle is connected to an electro-potential generator to create an over potential. In act 420 a substrate for a baffle, for example, a stainless steel plate, is positioned under the nozzle and connected to ground to create a zero potential in the substrate. In act 425 a first catalyst layer is formed on a surface of the substrate (without the use of a mesh or screen) by electrospraying. In act 430, the first catalyst layer undergoes a calcination process in an oven at a temperature of, for example, between about 450° C. and about 800° C. for a time period of, for example, four hours. The calcination temperature and time may vary depending upon the catalyst selected. In act 435 the second catalyst layer is formed on top of the first catalyst layer by electrospraying with the use of a mesh or screen to define a pattern of the second catalyst layer. In act 440 the second catalytic layer undergoes a calcination process. This calcination process may be at the same or a different time and/or temperature as the calcination process for the first catalyst layer. In act 445 the mesh or screen is lifted up and removed from the calcined second layer of catalyst. The patterned substrate may then be installed and used in a photocatalytic reactor.

Figure 5:
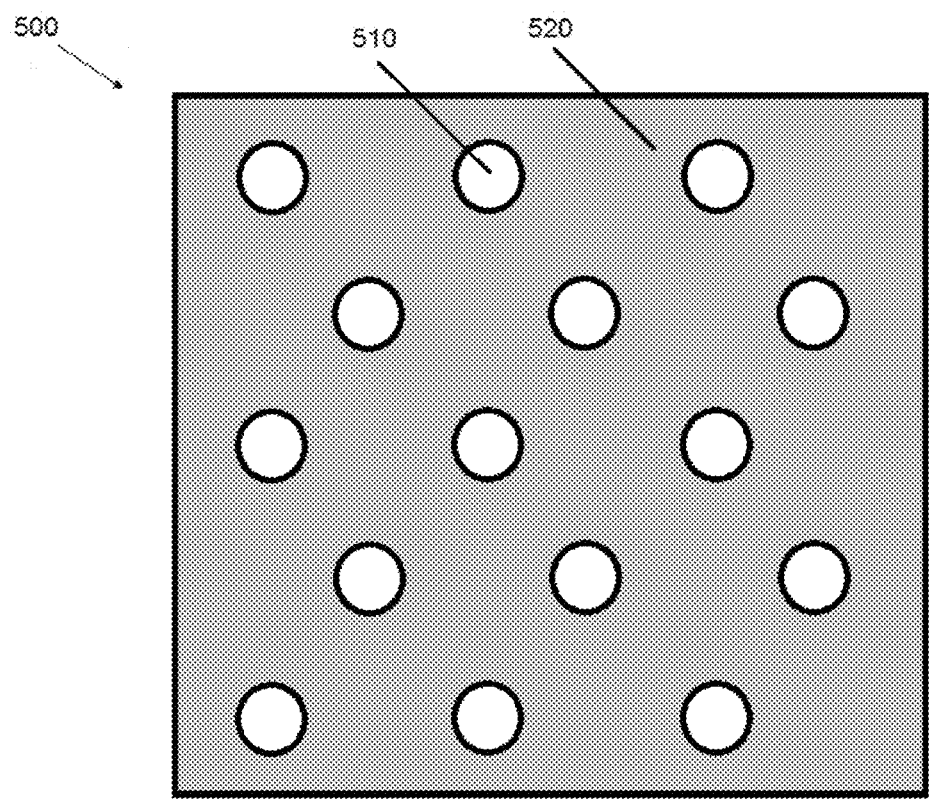
FIG. 5 is an illustration of another baffle which may be utilized in a reactor in accordance with an embodiment of the present disclosure.

In some embodiments, to enhance the distribution and minimize excessive energy being exposed to catalyst on surfaces of the baffles 145, the surface of the baffles 145 may be modified to include discrete elements 510 of reflective material, as in the baffle indicated generally at 500 in FIG. 5, where the passages for the UV lamps have been omitted for clarity. The presence of the discrete elements 510 of reflective material may even out the distribution of UV light onto the catalyst layer 520 and also reduce the amount of catalyst exposed to unnecessarily high amount of UV light, for example, in the central portion of the baffle. The number and positioning of the reflective material elements 510 may be adjusted accordingly to evenly distribute UV light energy across the different regions of the layer of catalyst on the baffle. The reflective material elements 510 may be in the shape of circles as illustrated in FIG. 5, or may be of alternate shapes, for example, squares or other polygons, or lines which may be straight, curved, discreet, or interconnected. The provision of the reflective material elements 510 on the baffles 415 may reduce the amount of unutilized and/or excessive UV energy directed onto some portions of the catalyst, for example, in processes where oxidation of contaminants is limited by the availability of catalytic surface area.

The patterns of catalyst and of reflective material described herein are only examples. Many different pattern designs are possible. Aspects of this disclosure are not limited to any specific pattern configurations.

Figure 6:
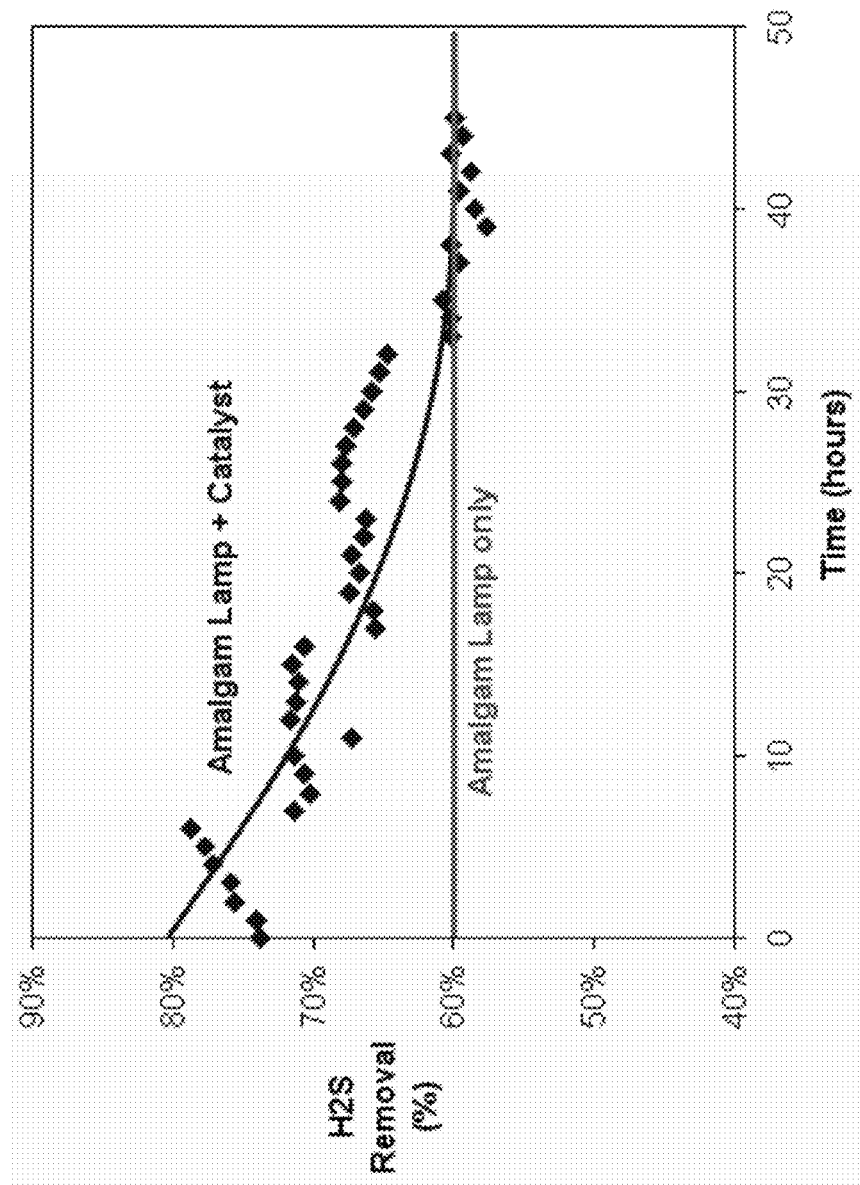
FIG. 6 is a graph illustrating the change in the effectiveness of a catalyst for the oxidation of $H_2S$ over time in a reactor in accordance with an embodiment of the present disclosure.

In some instances, it has been observed that a catalyst material, for example, $TiO_2$ may lose effectiveness over time. For example, as illustrated in FIG. 6, in an embodiment of a UV photocatalytic oxidation reactor, a $TiO_2$ catalyst exposed to air having a $H_2S$ concentration of between 50 pm and 60 ppm failed to exhibit any increased contaminant oxidation as compared to the use of UV irradiation alone after about 40 hours. Without being bound to a particular theory, it is believed that sulfate generated from the oxidation of $H_2S$ deposited on the catalyst surface over time, rendering the catalyst unavailable for contact with additional contaminant. Some embodiments of operating a UV reactor may thus include an act of periodically cleaning and/or regenerating surfaces of catalyst in the reactor.

Figure 7A:
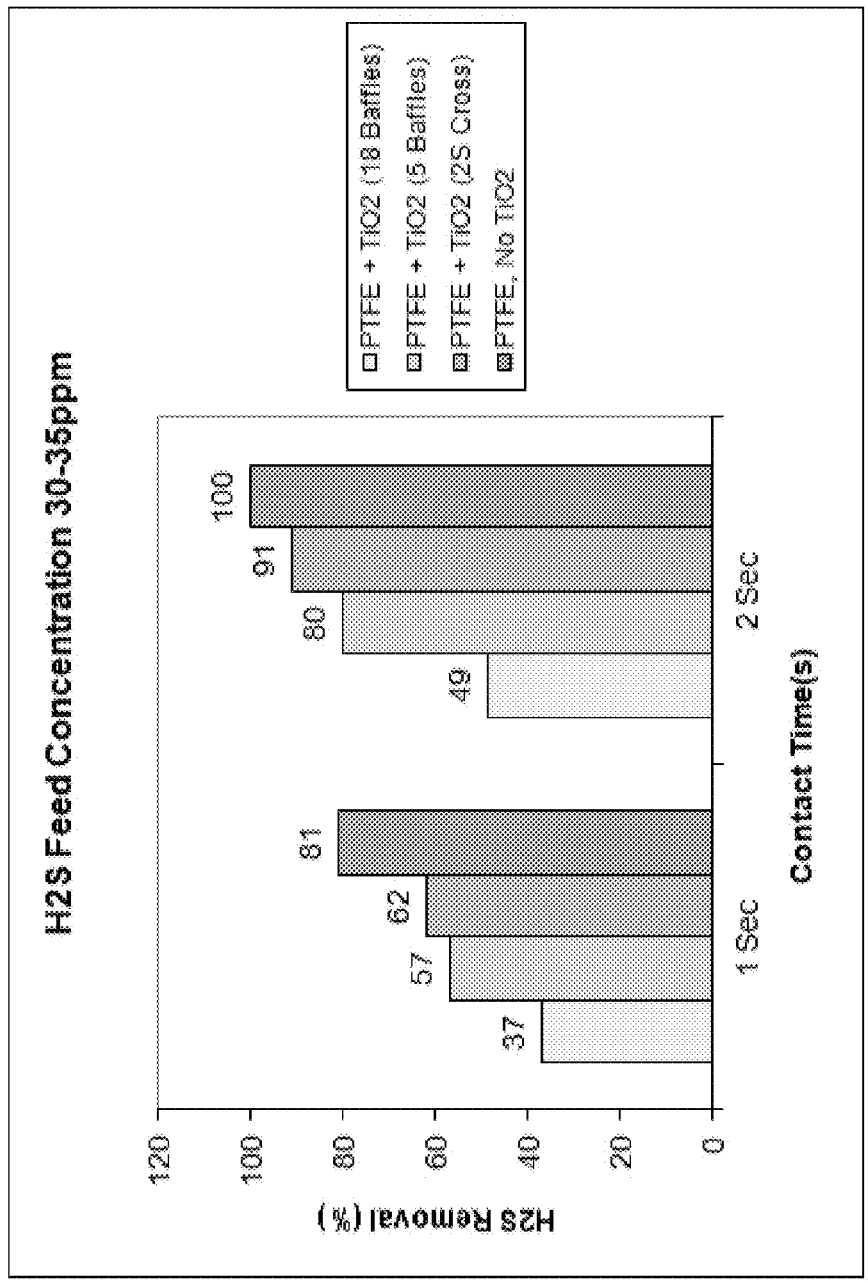
FIG. 7A is a graph illustrating the change in the $H_2S$ oxidation efficiency of a reactor in accordance with an embodiment of the present disclosure including various numbers of baffles when supplied with air having a concentration of $H_2S$ of between about 60 ppm and 70 ppm.

In some reactor designs, it has been observed that the removal efficiency of contaminants, for example, $H_2S$ in a UV photooxidation reactor is higher when the reactor does not include baffles. For example, as illustrated in FIGS. 7A ($H_2S$ supplied at a concentration of between 60 ppm and 70 ppm in air), 7B ($H_2S$ supplied at a concentration of between 30 ppm and 35 ppm in air), and 7C ($H_2S$ supplied at a concentration of between 60 ppm and 70 ppm in air), in some embodiments of a UV photooxidation reactor including UV reflective internal surfaces, the presence of baffles, even when coated with $TiO_2$ catalyst, reduces the $H_2S$ oxidation efficiency by about 50%. Without being bound to a particular theory it is believed that this reduction in contaminant oxidation efficiency is due to the baffles "shadowing" portions of the reactor from UV light generated from the UV lamps in the reactor. To at least partially alleviate the shadowing effect of the baffles, some embodiments of a UV reactor may include baffles which are substantially transparent to UV radiation, for example, transmitting greater than about 90% or in some embodiments, greater than about 99% of UV radiation. The UV transparent baffles may be formed of, for example, quartz glass and/or one or more UV transparent plastics, for example, poly(methyl methacrylate). To enhance the contaminant removal efficiency of the reactor, the UV transparent baffles may be coated with a layer of catalyst which is sufficiently thin to exhibit little, if any UV absorbance. The catalyst layer may have a thickness of, for example, between a monolayer of catalyst material and about 10 μm.

Figure 8:
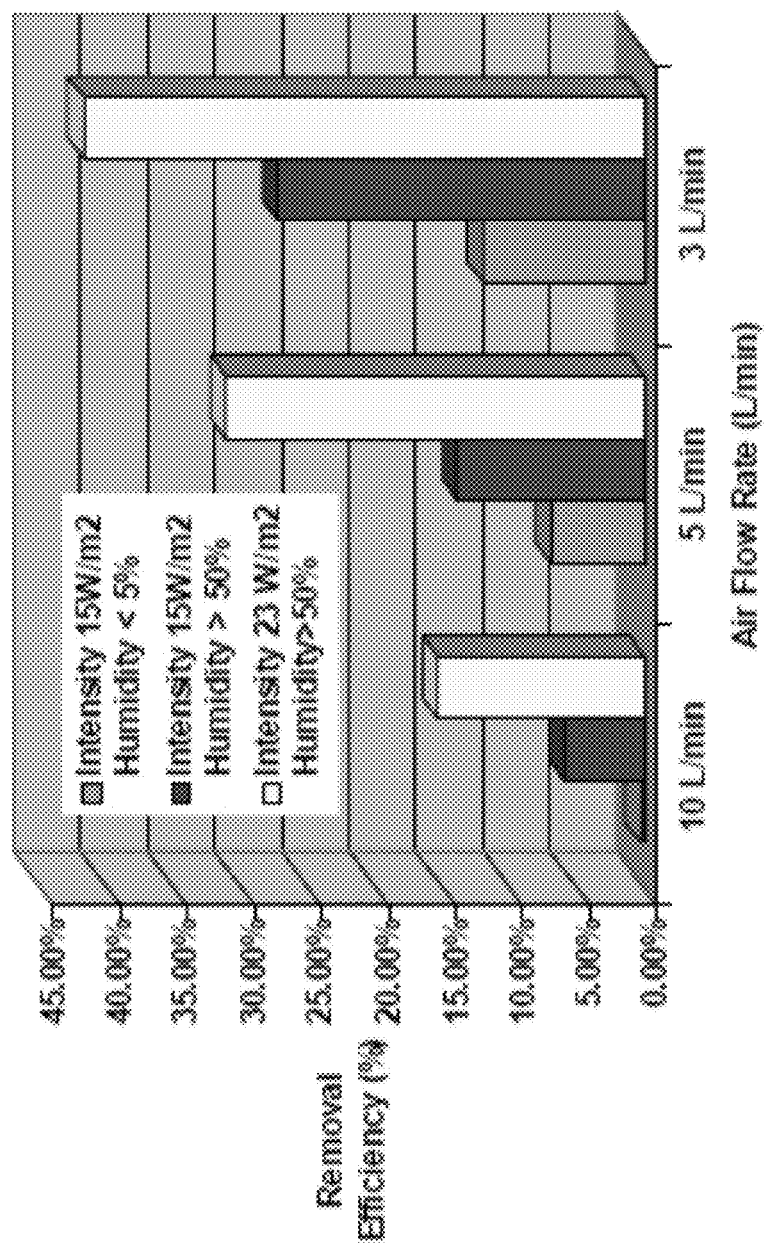
FIG. 8 is a graph illustrating the effect of humidity upon the oxidation efficiency of $H_2S$ in a reactor in accordance with the present disclosure.

A further method for enhancing the contaminant oxidation efficiency of a UV photooxidation reactor is to humidify air including the contaminants prior to introduction into the reactor. For example, as illustrated in FIG. 8, when the humidity of air including $H_2S$ at a concentration of between about 30 ppm and 50 ppm was increased from less than about 5% to greater than about 50%, the $H_2S$ removal efficiency at an air flow rate of 3 L/min and a UV intensity of 15 $W/m^2$ in an embodiment of a photooxidation reactor was observed to approximately double. In this example, the reactor used had a volume of 2,125 $cm^3$, a UV power of 7.3 W and included Degussa P25 $TiO_2$ nanoparticles as a catalyst.

Figure 9:
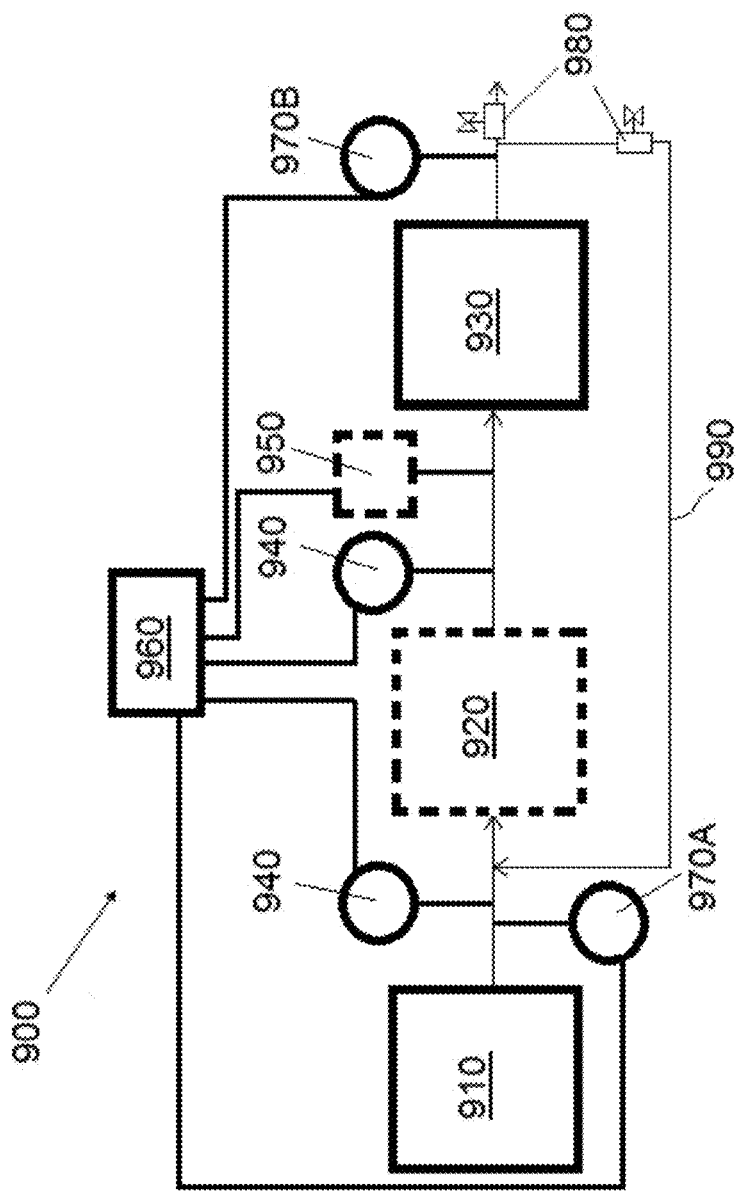
FIG. 9 illustrates a system in accordance with an embodiment of the present disclosure.

In some embodiments, a system for removing contaminants from air capitalizes on the effect of enhancement of contaminant oxidation efficiency with increased humidity. An embodiment of such a system is schematically illustrated in to FIG. 9, indicated generally at 900. The system 900 includes a source of contaminated air 910, for example, a refinery, a paper or pulp plant, or a wastewater or waste solids treatment plant or disposal site. A concentration of one or more contaminants in the contaminated air may be analyzed by a chemical analyzer 970A. The results of the analysis of the chemical analyzer 970A may be provided to a control system 960 which may adjust operating parameters of the system, for example, power level or air flow rate through the photooxidation reactor 930 responsive to the detected concentration of contaminant. Contaminated air from the source of contaminated air 910 is directed through a humidifier 920 and into the photooxidation reactor 930, which is in some embodiments a UV photooxidation reactor. Humidity monitors 940 may be present at various locations in the system, for example, upstream or downstream of the humidifier 920. The humidity monitors may provide feedback to the control system 960, which may be configured to adjust the amount of humidity provided by the humidifier to achieve a desired humidity in air entering the reactor 930. For example, if air exiting the source of contaminated air 910 is already sufficiently humid, for example, having a relative humidity of greater than about 85% at 21° C. or a relative humidity of greater than about 40% at 36.7° C. (about 0.16 kg moisture per kg of dry air), the humidifier may be deactivated. A source of humidity 950, for example, water vapor or steam may additionally or alternatively be provided to inject water vapor or steam into a conduit through which contaminated air flows to the reactor 930. Air exiting the photooxidation reactor 930 may be analyzed for the presence of remaining contaminants by a chemical analyzer 970B. If the concentration of remaining contaminants is outside an acceptable range, the control system may adjust operating parameters of the system, for example, increase or decrease a flow rate of contaminated air through the photooxidation reactor 930 or an amount of power delivered to a source of actinic radiation, for example, UV radiation in the photooxidation reactor 930 to bring the contaminant concentration to within an acceptable range. Air leaving the photooxidation reactor and containing an unacceptable level of contaminants may be redirected upstream of the photooxidation reactor through conduit 990 for additional treatment by the manipulation of valves 980. The acceptable upper limits for various contaminants in air output from the to system 900 may be dictated by local ordinances of a region in which the system 900 is operated. Exemplary upper limits for various contaminants are indicated in Table 1 below:

TABLE 1

Examples of upper limits for various airborne contaminants

| Contaminant | Acceptable concentration in air |
|---|---|
| $H_2S$ | less than about 0.01 ppm |
| Organic mercaptans and sulfides | less than about 0.01 ppm |
| Ammonia | less than about 5 ppm |
| Amines | less than about 0.01 ppm |

Example 1

Comparison of Different Reflective Coatings

Simulations were performed to calculate the effective average irradiance between baffle plates of a photooxidation reactor with different types of reflective material on the walls of baffle plates spaced 100 mm from each other and the internal walls of the reactor. A baseline model with 0% reflectance (a black body) exhibited an average of 1,070 $W/m^2$ irradiance produced from the UV lamps (6 UV lamps having a power rating of 30 W each) between the baffle plates. In a model where the baffle plates were constructed from polished stainless steel with a reflectance of 30%, the average irradiance increased to 1,320 $W/m^2$. In a model where the baffle plates included a reflective coating reflecting 99% of the UV light, the average irradiation between the plates increased to 1,890 $W/m^2$, an increase of 76% and 43%, respectively, as compared to that with the black body plates and the stainless steel plates.

Example 2

Comparison of Different Arrangements of Reflective Coatings

Simulations were performed to calculate the effective average irradiance between baffle plates of a reactor with reflective material added to different surfaces of the reactor. The simulated reactor had an internal volume of 18,000 $cm^3$, included 20 baffle plates equally spaced with a separation of 22.5 mm, and utilized seven UV lamps with a combined power output of 210 W. In a model where no reflective coating at all was applied to the reactor, the UV lamps produced an average irradiance of 220 $W/m^2$ between baffle plates. In a model where a reflective coating was applied to the internal walls of the reactor, the average irradiance between baffle plates increased to 241 $W/m^2$, an increase of 10% from the case where no reflective coating was used. In a model where the reflective coating was applied to the internal walls of the reactor and to one side of each baffle plate, the irradiance between baffle plates increased to 378 $W/m^2$, an increase of 78% from the case where no reflective coating was used.

Example 3

Figure 7B:
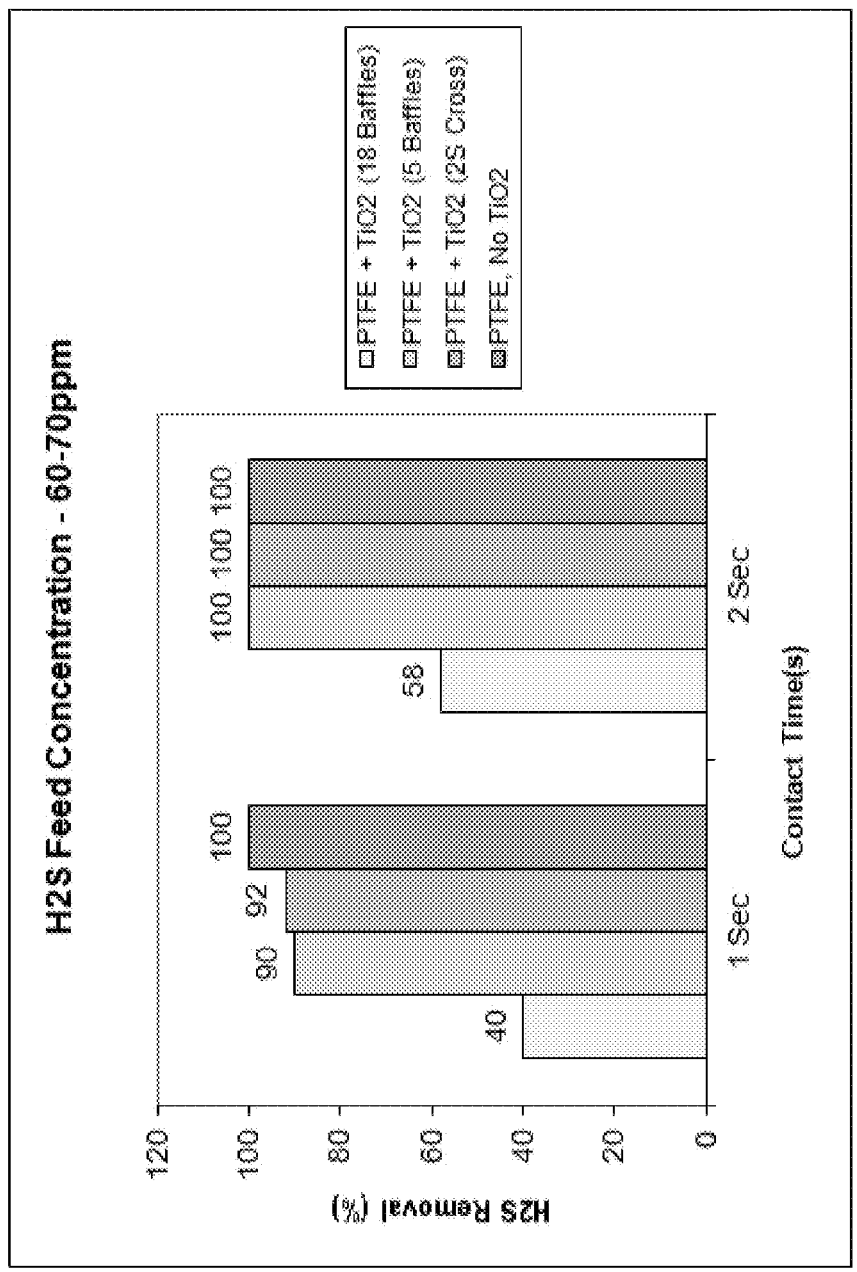
FIG. 7B is a graph illustrating the change in the $H_2S$ oxidation efficiency of a reactor in accordance with an embodiment of the present disclosure including various numbers of baffles when supplied with air having a concentration of $H_2S$ of between about 30 ppm and 35 ppm.
Figure 7C:
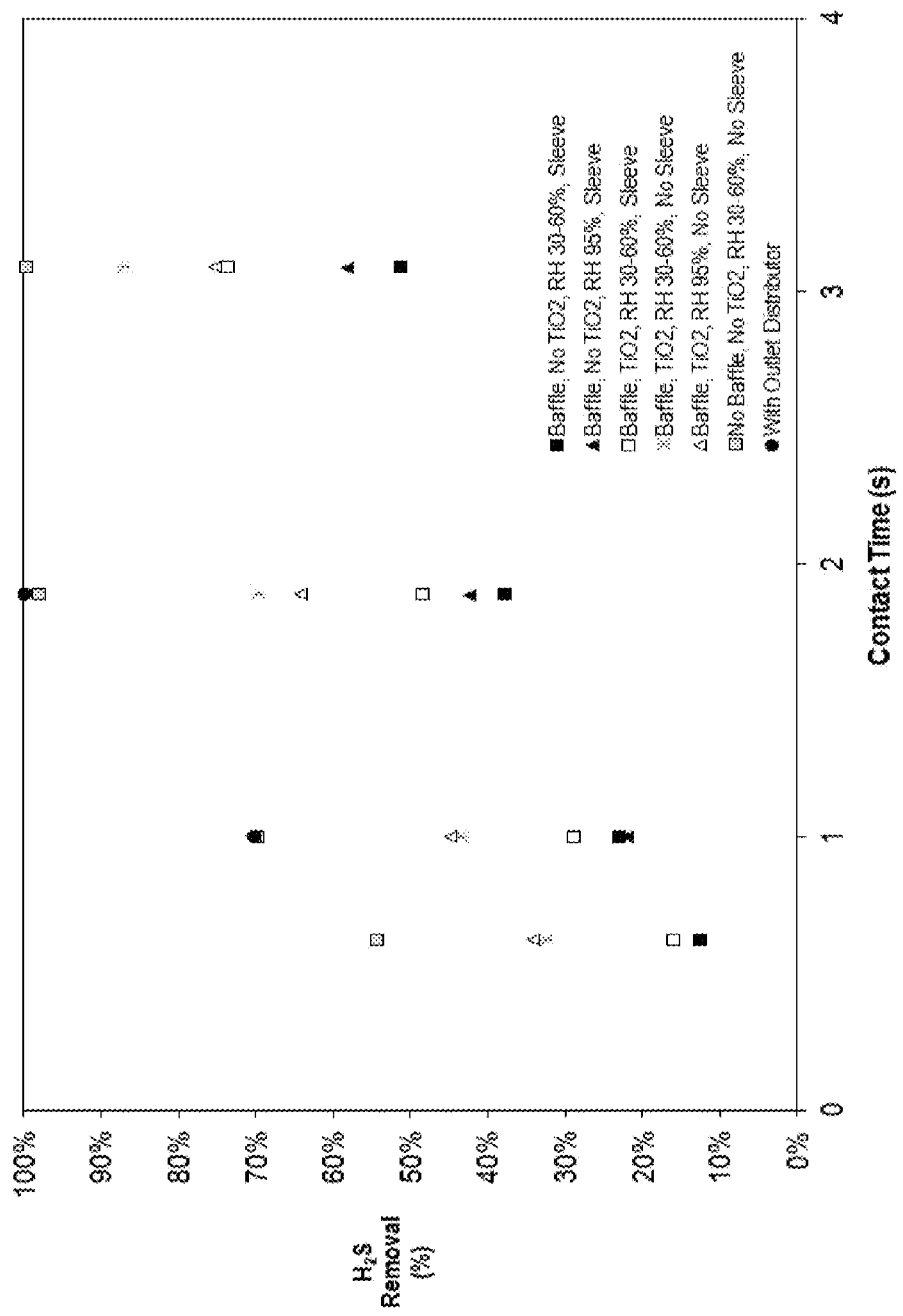
FIG. 7C is a graph illustrating the change in the $H_2S$ oxidation efficiency of a reactor in accordance with an embodiment of the present disclosure for various residence times of air in the reactor.

A UV oxidation reactor similar to that of FIG. 1A was evaluated for efficiency of oxidation of $H_2S$. The reactor had an internal volume of 18,000 $cm^3$ with no baffle plates and included six UV lamps with a total combined power of 180 W. Internal surfaces of the reactor were coated with a porous layer of reflective PTFE. When supplied with air having a concentration of $H_2S$ of between 60 ppm and 70 ppm, 81% of the $H_2S$ was oxidized when the air was flown through the reactor to provide a residence time of 1 second. When supplied with air having a concentration of $H_2S$ of between 60 ppm and 70 ppm, 100% of the $H_2S$ was oxidized when the air was flown through the reactor to provide a residence time of 2 seconds. (See FIG. 7A.) When supplied with air having a concentration of $H_2S$ of between 30 ppm and 35 ppm, 100% of the $H_2S$ was oxidized when the air was flown through the reactor to provide a residence time of 1 second. (See FIG. 7B.)

Having thus described several aspects of at least one embodiment of this disclosure, it is to be appreciated various alterations, modifications, and improvements will readily occur to those skilled in the art. Such alterations, modifications, and improvements are intended to be part of this dis- closure, and are intended to be within the spirit and scope of the disclosure. For example, although aspects of the present disclosure are described as used to remove biological floc from wastewater, these aspects may be equally applicable to the removal of any form of suspended solids, for example, inorganic suspended solids or fats, oil, or grease in a settling unit or vessel. Aspects of the wastewater treatment systems described herein may also use non-biological treatment methods rather than biological treatment methods for the treatment of wastewater. Accordingly, the foregoing description and drawings are by way of example only.

The phraseology and terminology used herein is for the purpose of description and should not be regarded as limiting. As used herein, the term "plurality" refers to two or more items or components. The terms "comprising," "including," "carrying," "having," "containing," and "involving," whether in the written description or the claims and the like, are open-ended terms, i.e., to mean "including but not limited to." Thus, the use of such terms is meant to encompass the items listed thereafter, and equivalents thereof, as well as additional items. Only the transitional phrases "consisting of" and "consisting essentially of," are closed or semi-closed transitional phrases, respectively, with respect to the claims. Use of ordinal terms such as "first," "second," "third," and the like in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

The invention claimed is:

1. An odor control system comprising:
    a source of air contaminated with a sulfur-containing compound; and
    a UV oxidation reactor having an inlet in fluid communication with the source of contaminated air, the reactor including:
        a source of UV radiation disposed within the reactor;
        a baffle including a pattern of photocatalyst features disposed on a surface of the baffle and discrete elements of reflective material disposed on the surface of the baffle; and
        a reflective coating disposed on internal surfaces of the reactor.

2. The system of claim 1, wherein the source of air comprises a wastewater treatment plant.

3. The system of claim 1, wherein the reflective coating comprises porous PTFE.

4. The system of claim 3, wherein the reflective coating has a reflectivity of greater than about 97% for UV radiation.

5. The system of claim 1, further comprising a humidifier configured to humidify the contaminated air prior to introduction of the contaminated air into the reactor.

6. The system of claim 1, wherein the source of UV radiation is a source of UV-C radiation.

7. The system of claim 6, wherein the sulfur-containing compound comprises $H_2S$.

8. The system of claim 7, wherein the source of UV-C radiation provides sufficient UV-C radiation to oxidize sufficiently all $H_2S$ in air having a concentration of $H_2S$ of between about 60 ppm and about 70 ppm within about two seconds.

9. The system of claim 1, wherein the baffle is substantially transparent to UV radiation.

10. The system of claim 9, wherein the photocatalyst is substantially transparent to UV radiation.

11. The system of claim 1, wherein the pattern of photocatalyst features includes a pattern of lines of the photocatalyst.

12. The system of claim 1, wherein the pattern of photocatalyst features includes a checker pattern of the photocatalyst.

13. A method of facilitating the oxidation of a sulfur-containing contaminant in air, the method comprising:
    providing a photooxidation reactor including:
        a source of actinic radiation disposed within the reactor;
        a baffle including a pattern of photocatalyst features disposed on a surface of the baffle and discrete elements of reflective material disposed on the surface of the baffle; and
        a reflective coating including porous PTFE disposed on internal surfaces of the reactor; and
    providing instructions to direct air contaminated with the sulfur-containing contaminant from a source of the contaminated air into the photooxidation reactor.

14. The method of claim 13, wherein providing the instructions comprises providing instructions to direct contaminated air from a wastewater treatment plant into the photooxidation reactor.

15. The method of claim 14, further comprising providing instructions to humidify contaminated air directed into the photooxidation reactor.

16. The method of claim 13, wherein providing the photooxidation reactor including the source of actinic radiation disposed within the reactor comprises providing the photooxidation reactor including a source of UV-C radiation disposed within the reactor.

17. The method of claim 13, further comprising providing instructions to monitor a concentration of the sulfur-containing contaminant in air output from the photooxidation reactor and to adjust an operating parameter of the photooxidation reactor responsive to the concentration of the sulfur-containing contaminant being above a predetermined set point.

18. A reactor for the oxidation of sulfur-containing contaminants in air with actinic radiation, the reactor comprising:
    an inlet and an outlet;
    a source of actinic radiation disposed within the reactor;
    a humidifier in fluid communication with the inlet;
    a baffle including discrete elements of reflective material disposed on a surface of the baffle; and
    a reflective coating including porous PTFE disposed on internal surfaces of the reactor.

19. The reactor of claim 18, wherein the baffle is substantially transparent to UV radiation.

20. The reactor of claim 19, wherein the baffle is at least partially coated with a layer of photocatalyst which is substantially transparent to UV radiation.

* * * * *